(12) United States Patent
Kang et al.

(10) Patent No.: US 11,338,134 B2
(45) Date of Patent: May 24, 2022

(54) SKIN TREATMENT DEVICE USING RF

(71) Applicants: JEISYS MEDICAL INC., Seoul (KR); Hyoung Moon Kim, Seoul (KR)

(72) Inventors: Dong Hwan Kang, Incheon (KR); Min Jung Shim, Seoul (KR); Hee Young Kim, Seoul (KR); Hyoung Moon Kim, Seoul (KR)

(73) Assignees: JEISYS MEDICAL INC., Seoul (KR); Hyoung Moon Kim, Seoul (KR)

( * ) Notice: Subject to any disclaimer, the term of this patent is extended or adjusted under 35 U.S.C. 154(b) by 0 days.

(21) Appl. No.: 17/254,858

(22) PCT Filed: Oct. 7, 2019

(86) PCT No.: PCT/KR2019/013098
§ 371 (c)(1),
(2) Date: Dec. 22, 2020

(87) PCT Pub. No.: WO2021/015359
PCT Pub. Date: Jan. 28, 2021

(65) Prior Publication Data
US 2021/0196951 A1 Jul. 1, 2021

(30) Foreign Application Priority Data
Jul. 24, 2019 (KR) .................. 10-2019-0089745

(51) Int. Cl.
*A61N 1/32* (2006.01)
*A61N 1/36* (2006.01)
*A61N 1/05* (2006.01)

(52) U.S. Cl.
CPC .......... *A61N 1/328* (2013.01); *A61N 1/0502* (2013.01); *A61N 1/36017* (2013.01); *A61N 1/36034* (2017.08)

(58) Field of Classification Search
CPC ................ A61N 1/328; A61N 1/36034; A61N 1/36017; A61N 1/0502
See application file for complete search history.

(56) References Cited

U.S. PATENT DOCUMENTS

2007/0142885 A1* 6/2007 Hantash .................. A61N 1/06
607/102
2017/0209695 A1 7/2017 Solomon
(Continued)

FOREIGN PATENT DOCUMENTS

KR 20-0173776 Y1 3/2000
KR 10-2016-0038566 A 4/2016
(Continued)

OTHER PUBLICATIONS

International Search Report for PCT/KR2019/013098 dated Apr. 23, 2020 from Korean Intellectual Property Office.
(Continued)

*Primary Examiner* — Unsu Jung
*Assistant Examiner* — Adreanne A. Arnold
(74) *Attorney, Agent, or Firm* — Revolution IP, PLLC

(57) ABSTRACT

A skin treatment device includes: an RF generator configured to generate an RF output; and an applicator being of a bipolar type and including an applicator body and needles, wherein the needles are arranged on a front surface of the applicator body, inserted into a dermal layer of the skin of a person to be treated and electrically connected to the RF generator to transmit the RF output, wherein, when the applicator is turned on, the applicator transmits a single or a plurality of RF pulses according to the RF output to the person to be treated, and the RF output is 5 W or more and 13 W or less, and a frequency of the RF output is greater than
(Continued)

1 MHz and less than 3 MHz, and a duration of the RF pulse according to the RF output is 50 ms or more and 100 ms or less.

6 Claims, 9 Drawing Sheets

(56) References Cited

U.S. PATENT DOCUMENTS

2019/0059992 A1   2/2019  Ko et al.
2020/0155839 A1*  5/2020  Seo ..................... A61M 37/00

FOREIGN PATENT DOCUMENTS

| | | | | |
|---|---|---|---|---|
| KR | 10-2017-0019024 A | | 2/2017 | |
| KR | 10-2017-0086461 A | | 7/2017 | |
| KR | 10-2019-0022102 A | | 3/2019 | |
| KR | 20190022102 A | * | 3/2019 | ......... A61B 18/1477 |
| WO | 2007/099460 A2 | | 9/2007 | |
| WO | WO-2007099460 A2 | * | 9/2007 | ......... A61B 18/1206 |

OTHER PUBLICATIONS

Office Action of Japanese Patent Application No. 2020-573265 dated Mar. 8, 2022.

* cited by examiner

FIG. 10
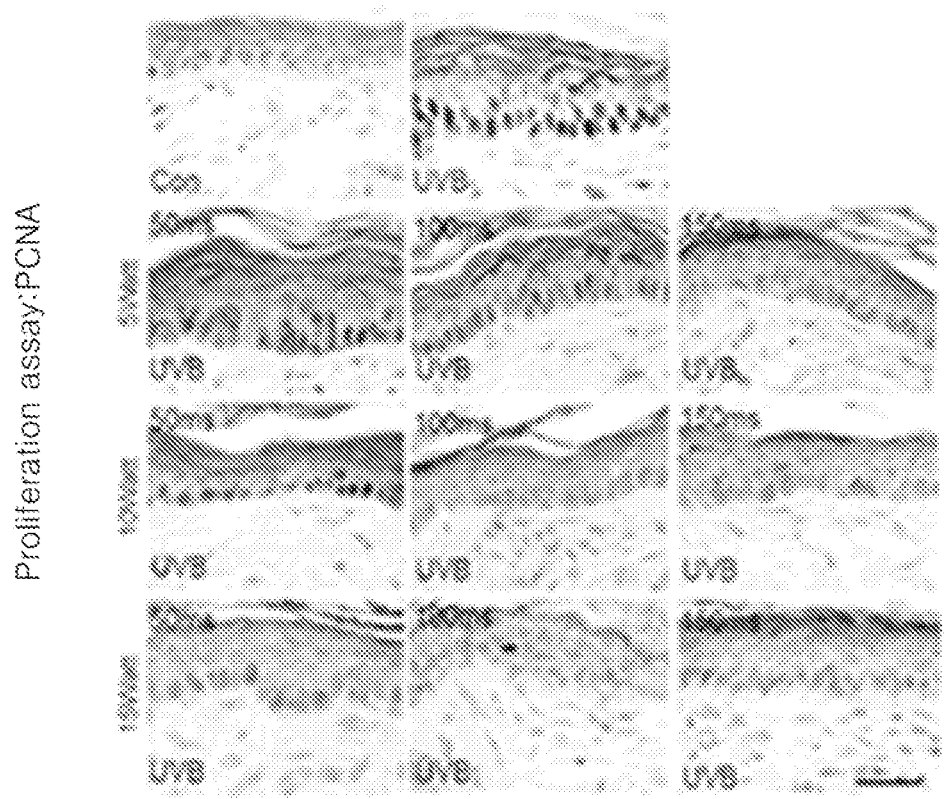
(a)
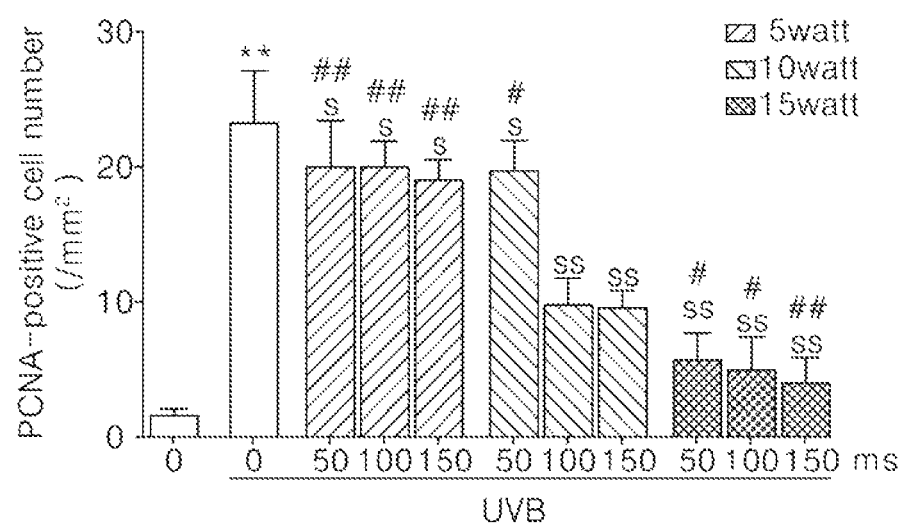
(b)

SKIN TREATMENT DEVICE USING RF

TECHNICAL FIELD

The present invention relates to a skin treatment device using a radio frequency (RF), which is capable of effectively treating pigmentation of the skin.

BACKGROUND ART

Various methods have been used to improve pigmentation. Methods using energy based devices include intense pulsed light (IPL) and laser. Methods using drugs include vitamin C, tretinoin, and hydroquinone. In addition, glycolic acid peeling, TCA peeling, and phenol peeling have been used as chemical peeling.

Among them, the most popular lasers have been used, and the types thereof are Nd:YAG laser toning, factional laser, dye/yellow laser, and long pulsed Nd:YAG. However, there is a fatal disadvantage that many problems occur in the treatment of pigmentation using laser.

First, inflammatory pigmentation (post inflammatory hyperpigmentation (PIH)) and hyperpigmentation. As the skin becomes inflamed, melanin is excessively produced to protect it, resulting in brown or dark red pigmentation of a treatment site. This is due to the excessively large energy of the laser, and because the photon energy is 1 to 3 eV, it causes thermal damage to a deeper part of a skin layer where surrounding tissues and pigments are located, causing an inflammatory reaction. Cells (melanophage) are formed by lodging in a deep layer of the skin.

Second, it is hypopigmentation. It is a symptom that occurs when melanin in the treatment site is relatively insufficient compared to the surrounding skin, and the treatment site becomes excessively whiter than the surrounding tissues. It is caused by the destruction of melanocytes that produce melanin as too much energy is transmitted into the skin with the high energy of the laser. There is a fatal problem that recovery is difficult, and it often occurs when the number of laser treatments is large.

In addition, IPL has a wide wavelength range and has a high overall energy, but has a relatively low intensity of specific energy required for melasma treatment, so there is a limit to melasma treatment. In addition, there is a problem of destroying surrounding cells by applying a relatively large amount of energy.

DETAILED DESCRIPTION OF THE INVENTION

Technical Problem

The present invention provides a skin treatment device using a radio frequency (RF), which is capable of effectively treating pigmentation of the skin.

Technical Solution

According to an aspect of the present invention, there is provided a skin treatment device using an RF, the skin treatment device including an RF generator configured to generate an RF output and an applicator being of a bipolar type and including an applicator body and needles, wherein the needles are arranged on a front surface of the applicator body, inserted into a dermal layer of the skin of a person to be treated and electrically connected to the RF generator to transmit the RF output, wherein, when the applicator is turned on, the applicator transmits a single or a plurality of RF pulses according to the RF output to the person to be treated, and the RF output is 5 W or more and 13 W or less, and a frequency of the RF output is greater than 1 MHz and less than 3 MHz, and a duration of the RF pulse according to the RF output is 50 ms or more and 100 ms or less.

The number of the needles may be 16 or more and 49 or less, and the skin invasion depth of the needles may be greater than 0 mm and 1 mm or less.

A frequency of the RF output may be 2 MHz.

Effects of the Invention

In a skin treatment device using a radio frequency (RF) according to the present invention, pigmentation of the skin can be greatly reduced using an RF output.

DESCRIPTION OF THE DRAWINGS

FIG. 10 shows a result of observing the level at which the proliferation of melanocytes cells is inhibited through chemical staining called proliferation assay (PCNA) in a mouse animal experiment HRM2.

MODE OF THE INVENTION

Hereinafter, embodiments of the present invention will be described as below with reference to the attached drawings.

Figure 1:
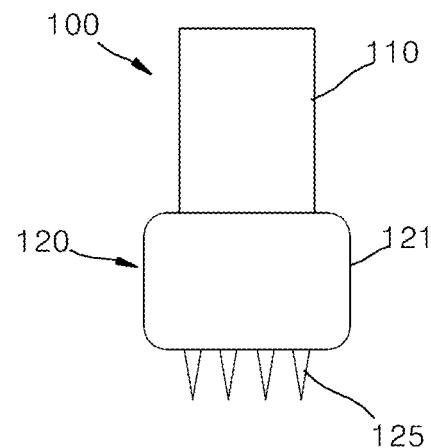
FIG. 1 is a view of the configuration of a skin treatment device using a radio frequency (RF) according to an embodiment of the present invention.

Referring to FIG. 1, a skin treatment device 100 using a radio frequency (RF) according to an embodiment of the present invention is shown. The skin treatment device 100 using an RF includes an RF generator 110 and an applicator 120. The RF generator 110 performs a function of generating an RF output. Various known devices for generating an output required in the present embodiment may be used as the RF generator.

The applicator 120 includes an applicator body 121 and needles 125. The applicator 120 is formed to be gripped by a user (a doctor, etc.), and includes various manipulation units (not shown) such as an on/off switch (not shown) and RF output settings. The applicator 120 is of a bipolar type.

The needles 125 are arranged on the front surface of the applicator body 121. The needles 125 are formed of conductive materials and are electrically connected to the RF generator 110 to transmit the RF output. The RF output is transmitted to the skin of a person to be treated as RF pulses having various shapes such as a rectangular shape.

Before the applicator 120 is operated (turned on), the applicator 120 is inserted into the dermal layer of the skin of the person to be treated. To this end, the approximate insertion depth of the needles 125 is 1 mm or less (that is, 0<invasion depth 1 mm). However, the present invention is not limited thereto. In addition, the number of the needles 125 is 16 to 49, but the present invention is not limited thereto.

Figure 2:
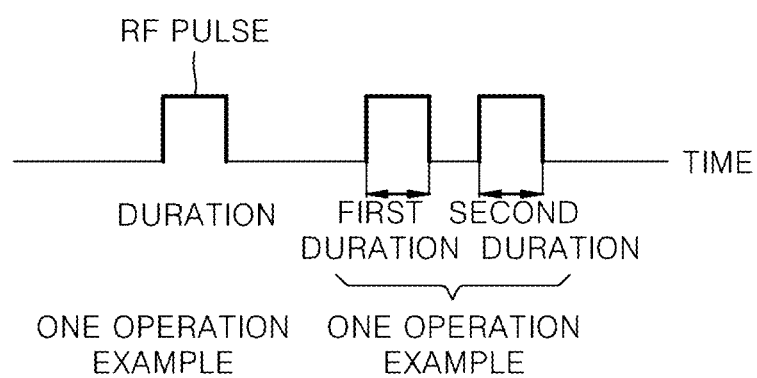
FIG. 2 illustrates an embodiment of an RF output transmitted to the skin from the skin treatment device using an RF of FIG. 1.

When the applicator 120 is turned on, the applicator 120 transmits a single or a plurality of RF pulses according to the RF output to the person to be treated, and then the applicator is automatically turned off. FIG. 2 shows an embodiment of the RF pulse.

Referring to FIG. 2, when the applicator is operated once (between on and off), one RF pulse or two RF pulses are generated and transmitted to the skin of the person to be treated. In the present invention, a duration of the RF pulse refers to a duration of a pulse applied to the skin in one operation of the applicator (the duration of a single pulse in the case of the single pulse, and the sum of the durations in the case of multiple pulses (the first duration and the second duration)). However, the present invention is not limited thereto, and when the applicator is operated once, three or more RF pulses may be generated and transmitted to the skin of the person to be treated.

In the skin treatment device using an RF, the condition of the RF output is set through the following experiment and analysis in order to optimize the skin pigmentation effect of the person to be treated.

Figure 3:
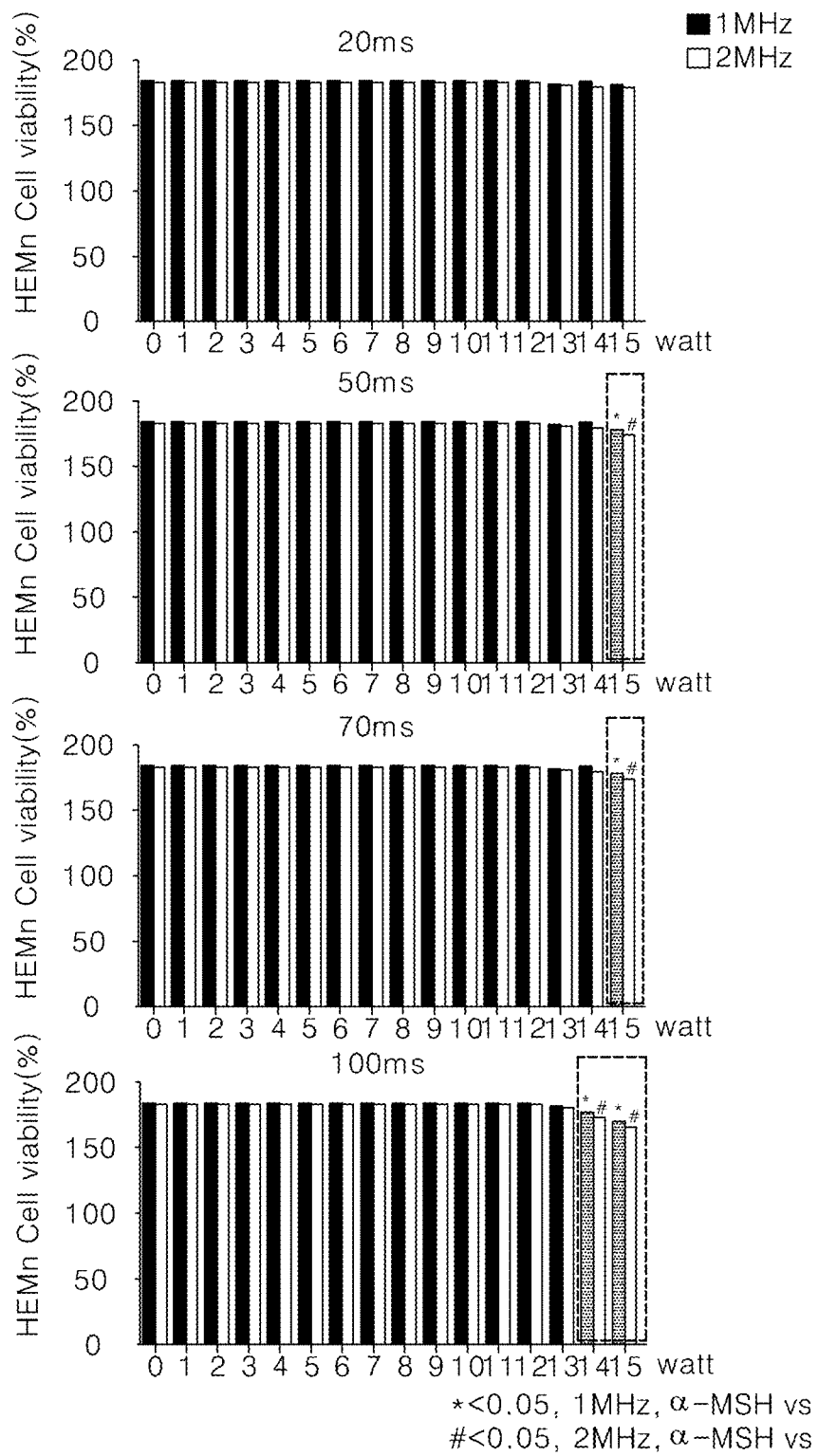
FIGS. 3 and 4 are graphs showing an experimental result of cell viability using the skin treatment device using an RF of FIG. 1.
Figure 4:
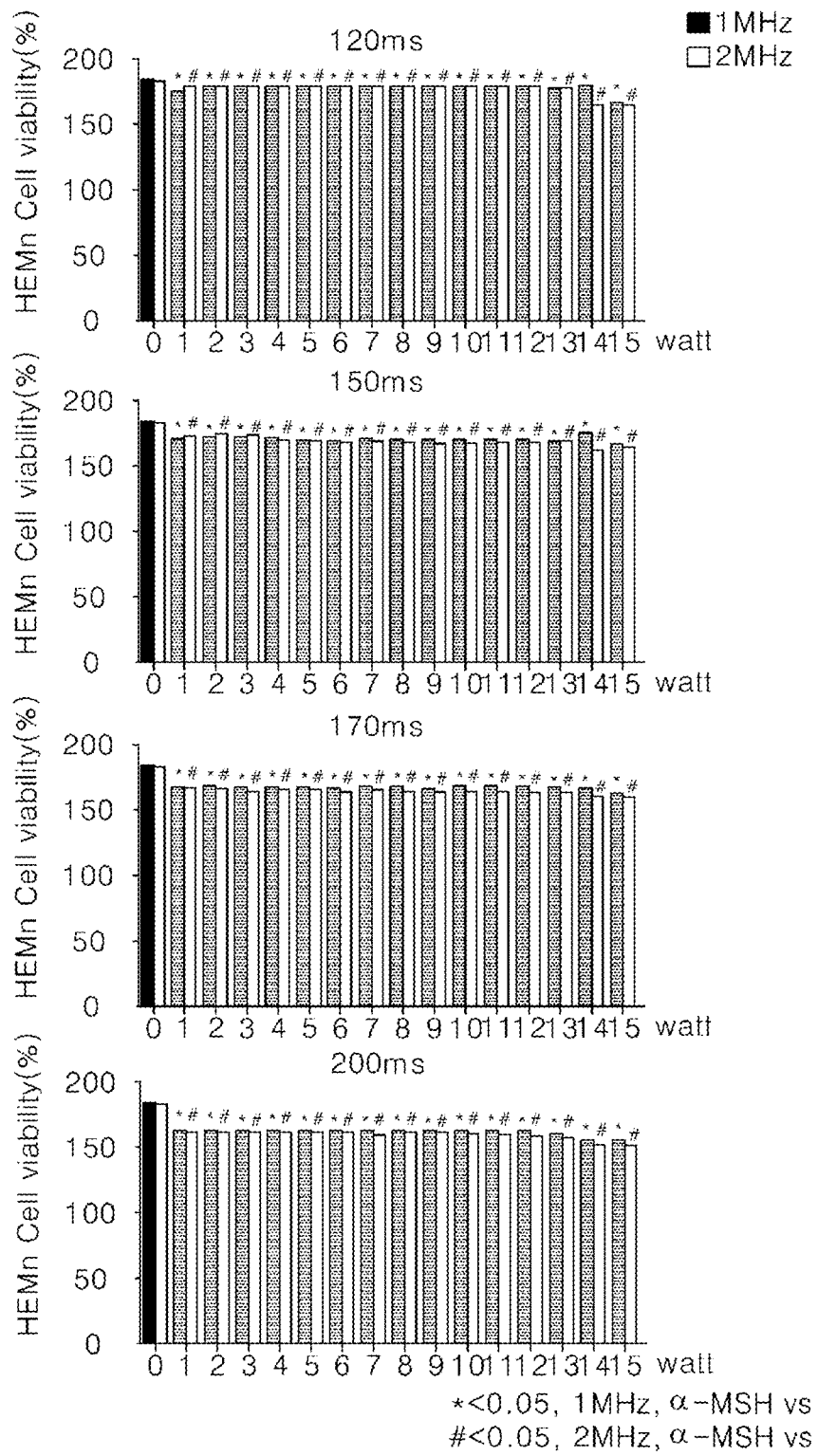

FIGS. 3 and 4 show graphs of the results of conducting a human primary melanocyte (HEMn) cell viability experiment using the skin treatment device using an RF.

In this experiment, setting parameters of the RF output are RF output (Watt, W), RF frequency (Hertz, MHz), and the duration of the RF pulse. A test subject is $1\times10^4$ cells, and the present experiment was performed to confirm the conditions in which cells die. Here, HEMn Cell Viability (%) means cell viability.

In addition, in FIGS. 3 and 4, cell viability is shown at 1 MHz and 2 MHz of the RF output for a specific pulse duration. One RF pulse was applied to the test subject for 1 day, and the RF output was performed in 1 W units from 1 W to 15 W, and the duration of the RF pulse was 20 ms, 50 ms, 70 ms, 100 ms, 120 ms, 150 ms, 170 ms, and 200 ms. The number of needles was 16.

As a result of the experiment, it can be seen that, regardless of the RF output, when the duration of the RF pulse is 120 ms or more (see FIG. 4), cell viability is greatly reduced. In addition, when the duration of the RF pulse is 50 ms and 70 ms and the RF output is 15 W or more, cell viability is greatly reduced, and when the duration of the RF pulse is 100 ms and the RF output is 14 W or more, cell viability is significantly reduced (see FIG. 3).

From these experimental results, preferably, the frequency of the RF output is selected to be less than 1 MHz and less than 3 MHz, the duration of the RF pulse is selected to be 100 ms or less, and the RF output is selected to be 13 W or less.

Figure 5:
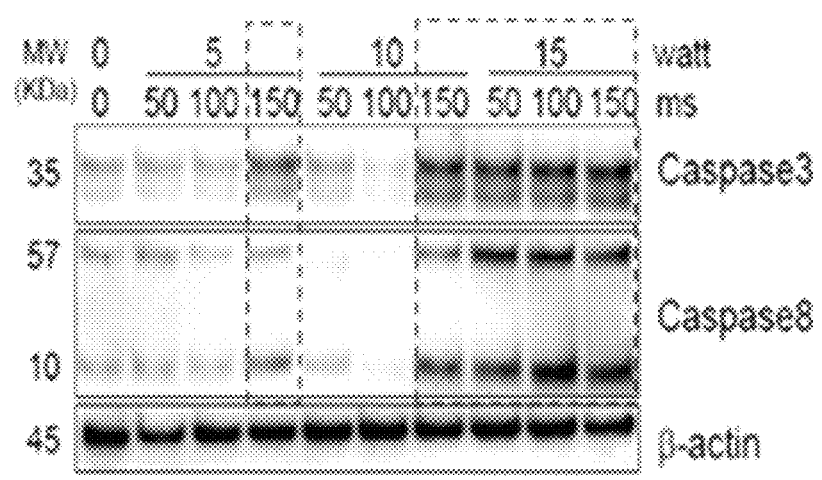
FIG. 5 is a graph showing a result of an HRM2 cell death animal experiment.

FIG. 5 shows a result of an HRM2 cell death animal experiment, and when the duration of the RF pulse is 150 ms or more or the RF output is 15 W or more, it can be seen that a cell death rate is significantly increased (however, the case where the RF duration is 20 ms and at the same time the RF output of 15 W is not included).

Figure 6:
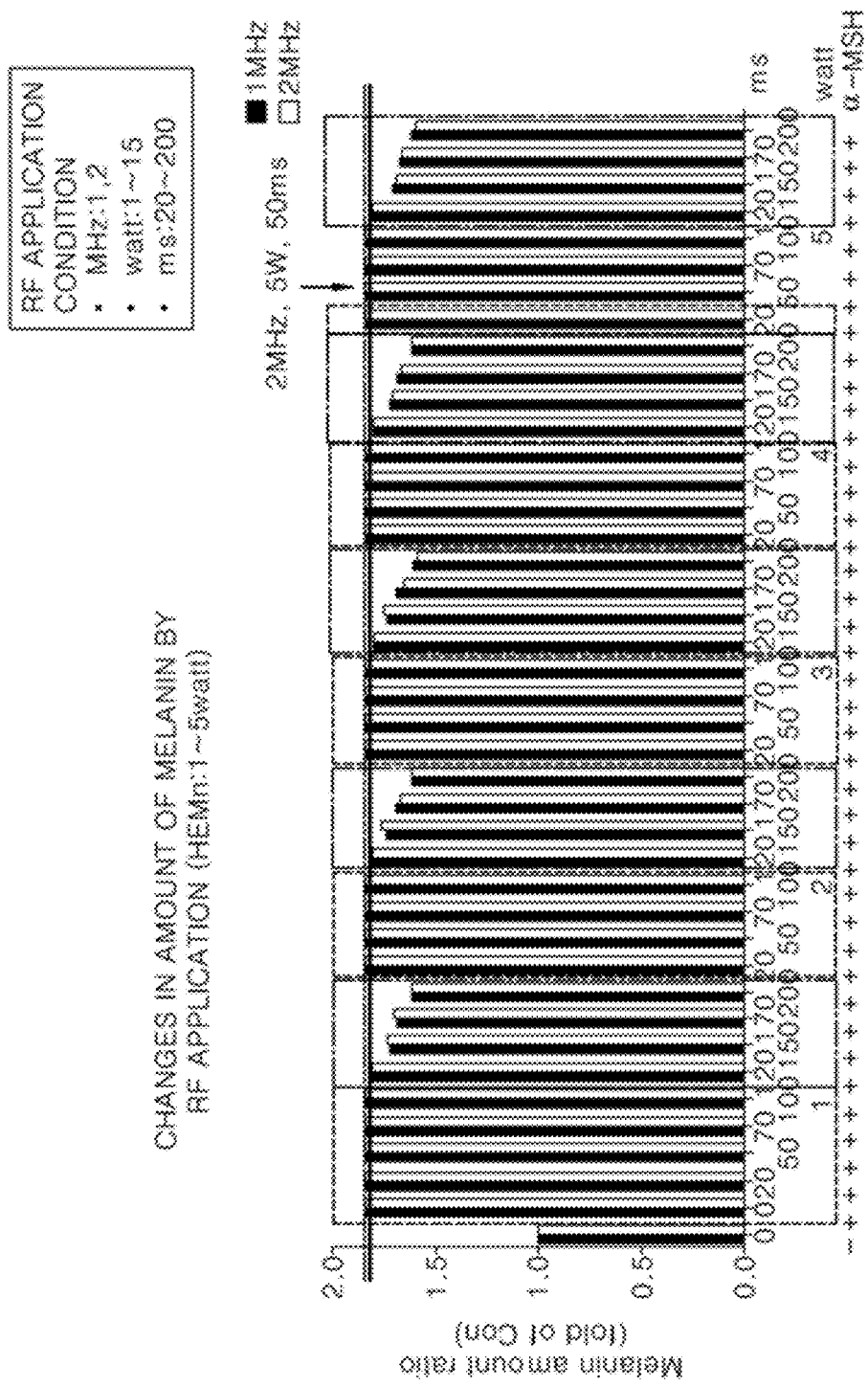
FIGS. 6 through 8 are graphs showing an experimental result for measuring a decrease in the amount of melanin using the skin treatment device using an RF of FIG. 1.
Figure 7:
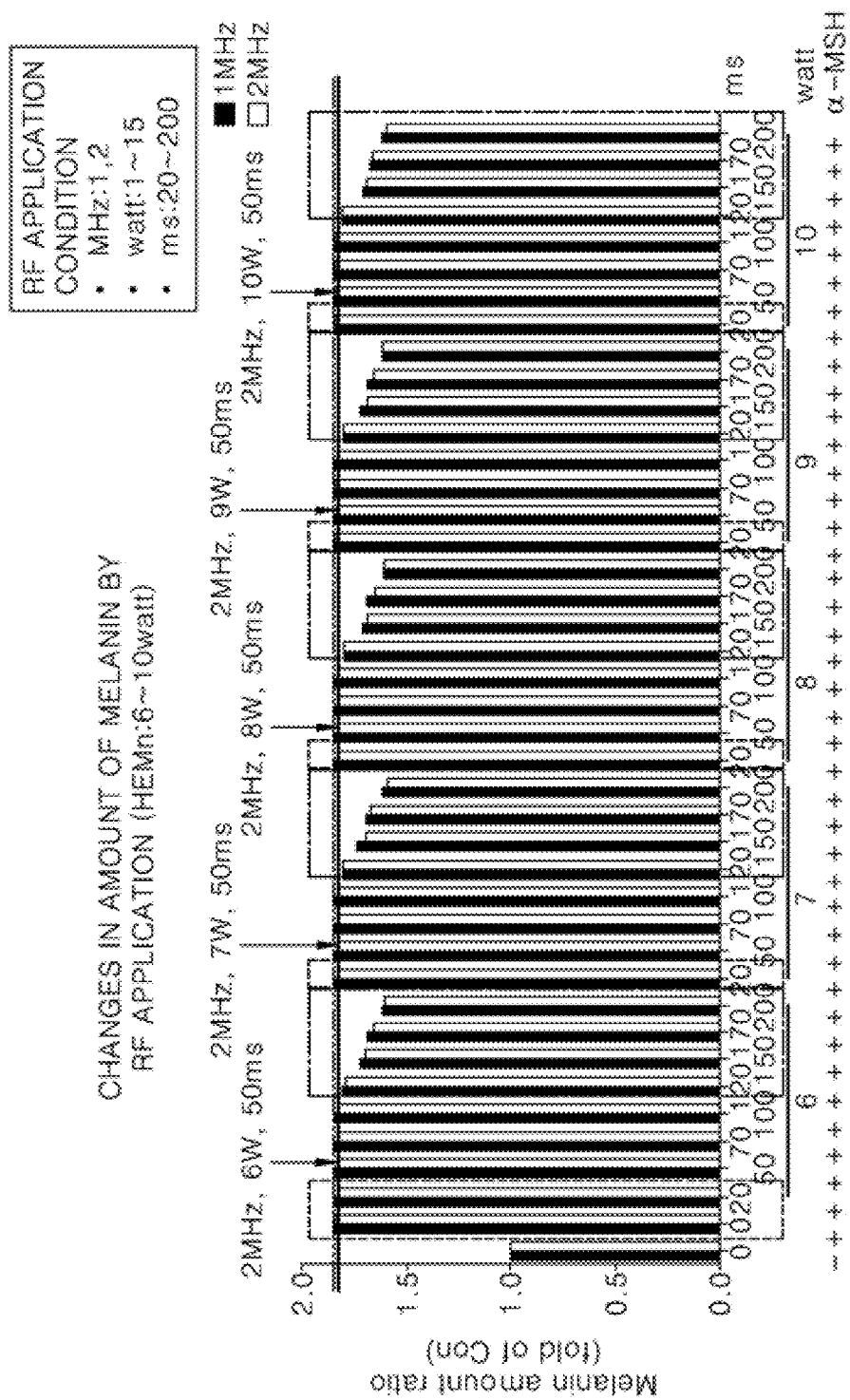
Figure 8:
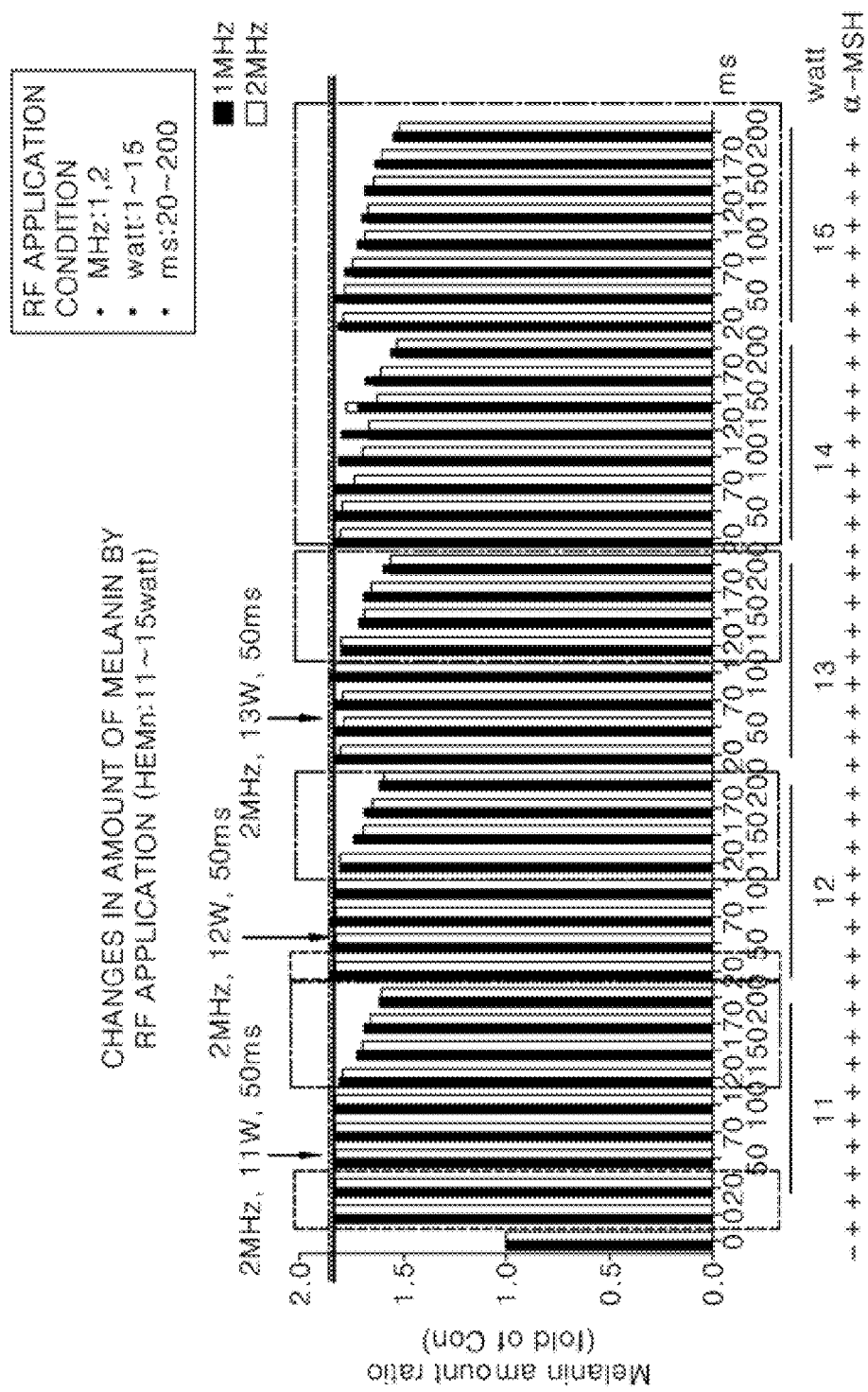

Referring to FIGS. 6 through 8, as an experiment for measuring the decrease in the amount of melanin, it is a Melanin assay experiment. As for HEMn, the test subject is $1\times10^4$ cells. Here, the melanin amount ratio means the ratio of the amount of melanin.

FIGS. 6 through 8 show results of applying one RF pulse to a test subject for one day. An RF output was performed from 1 W to 15 W per 1 W unit, and the duration of the RF pulse was performed in 20 ms, 50 ms, 70 ms, 100 ms, 120 ms, 150 ms, 170 ms, and 200 ms. The number of needles was 16.

As a result of the experiment, it was confirmed that the amount of melanin significantly decreased when the RF output was 5 W or more, the RF duration was 50 ms or more, and the RF frequency was greater than 1 MHz.

In this way, through the human primary melanocyte (HEMn) cell viability experiment and the decrease in the amount of melanin, when the RF output is 5 W or more and 13 W or less, the frequency of the RF output is greater than 1 MHz and less than 3 MHz and the duration of the RF pulse by the RF output is 50 ms or more and 100 ms or less, it is derived that the pigmentation of the skin can be effectively treated.

Figure 9:
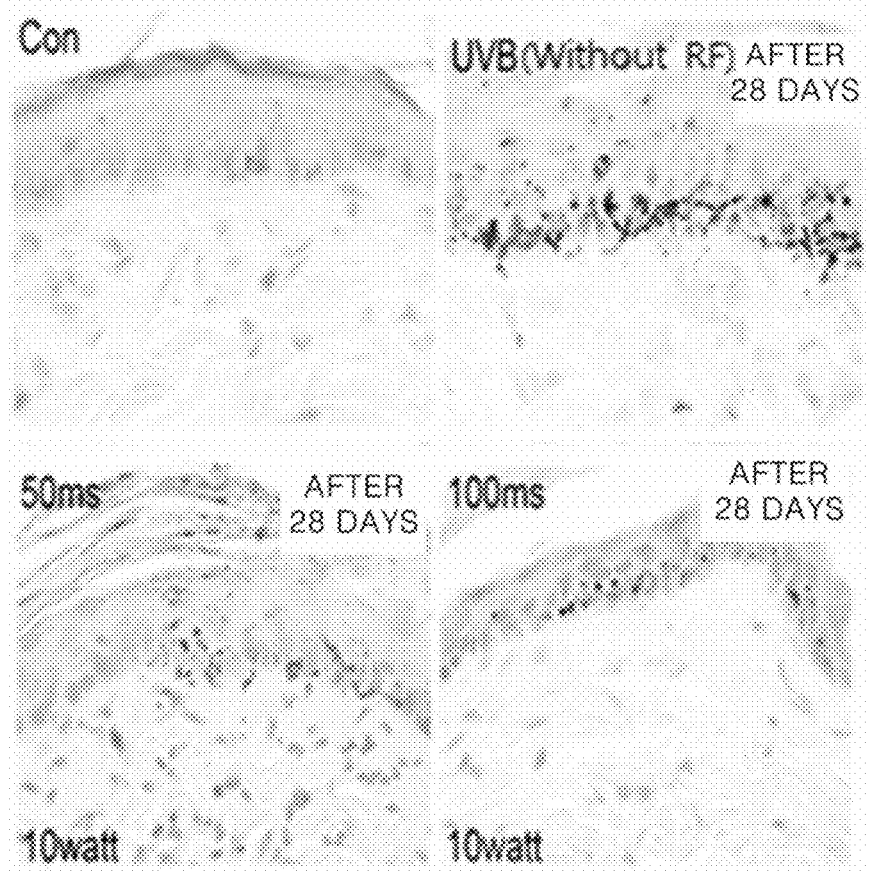
FIG. 9 is a photograph of an experiment result showing the result of irradiating the pigmented mice once with an RF pulse of the skin treatment device using an RF of FIG. 1, and then irradiating UV once every two days for 28 days.

FIG. 9 is a photograph of the experimental results showing the result of irradiating the pigmented mice with an RF pulse once, and then irradiating UV once every two days for 28 days. In FIG. 9, a second picture from the left shows a state of irradiation with UV without RF application, and third and fourth pictures show a state in which 50 ms and 100 ms of RF of 10 W are applied, respectively. As a result of the experiment, when RF was applied, the melanin significantly decreased, and the decrease at 100 ms was greater.

FIG. 10 is a result of observing the level at which the proliferation of melanocytes cells is inhibited through a chemical staining called proliferation assay (PCNA) in a mouse animal experiment HRM2.

Referring to the tissue pictures of (a) of FIG. 10, compared to the tissue picture on the top right (Comparative example), in the tissues corresponding to the RF output of 5 W or more and less than 15 W and the RF pulse duration 50 ms to 100 ms, it can be seen that the outer surface of the skin and the area where the melanocytes are located are lighter in brown. This means that the proliferation of melanocytes was inhibited. In the tissues corresponding to one of conditions that the RF output is 15 W and the RF duration is 150 ms, cell proliferation is inhibited to the extent that the tissues are hardly brownish, but this is a range where cell death occurs and thus is not considered as an effect.

(b) of FIG. 10 shows data obtained by quantifying the results of (a) of FIG. 10. The black bar graph marked "0" on the horizontal axis means the same group as the UVB tissue picture of the PCNA tissue. As described above, it is shown that cell proliferation was inhibited when the RF output was 5 W or more and less than 15 W and the RF pulse duration was 50 to 100 ms compared to the black bar graph. However, in a group corresponding to one of the conditions that the RF output was 15 W or the RF duration was 150 ms, cell proliferation was further inhibited in the corresponding group, but this is a condition in which cell death occurs and thus is not considered as an effect.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

By using the present invention, a skin treatment device using a radio frequency (RF), which is capable of effectively treating pigmentation, can be manufactured.

The invention claimed is:

1. A skin pigmentation reducing device using a radio frequency (RF), the skin treatment device comprising:
   a RF generator configured to generate an RF output; and
   an applicator being of a bipolar type and including an applicator body and needles, wherein the needles are arranged on a front surface of the applicator body, configured to be inserted into a dermal layer of the skin of a person to be treated and electrically connected to the RF generator to transmit the RF output,
   wherein, when the applicator is turned on, the applicator transmits a single or a plurality of RF pulses according to the RF output to the person to be treated,
   a frequency of the RF output is only in a range of greater than 1 MHz and less than 3 MHz so as to reduce pigmentation of the skin according to the RF output,
   the RF output is only in a range of 5W to 13W, wherein the range of 5W or more increases an amount of decrease in melanin and the range of 13W or less prevents a decrease in viability of melanocytes, and
   a duration of the RF pulse according to the RF output is only in a range of 50 ms to 100 ms, wherein the range of 50 ms or more increases an amount of decrease in melanin and the range of 100 ms or less to prevent a decreases in viability of melanocytes.

2. The skin pigmentation reducing device of claim 1, wherein the number of the needles are 16 or more and 49 or less, and the skin invasion depth of the needles is 1 mm or less.

3. The skin pigmentation reducing device of claim 1, wherein a frequency of the RF output is 2 MHz.

4. A skin pigmentation reducing device using a radio frequency (RF), the skin treatment device comprising:
   a RF generator configured to generate an RF output; and
   an applicator being of a bipolar type and including an applicator body and needles, wherein the needles are arranged on a front surface of the applicator body, configured to be inserted into a dermal layer of the skin of a person to be treated and electrically connected to the RF generator to transmit the RF output,
   wherein, when the applicator is turned on, the applicator transmits a single or a plurality of RF pulses according to the RF output to the person to be treated,
   the RF output is only in a range of 5W to 13W,
   a frequency of the RF output is only in a range of greater than 1 MHz and less than 3 MHz, and
   a duration of the RF pulse according to the RF output is only in a range of 50 ms to 100 ms.

5. The skin pigmentation reducing device of claim 4, wherein the number of the needles are 16 or more and 49 or less, and the skin invasion depth of the needles is 1 mm or less.

6. The skin pigmentation reducing device of claim 4, wherein a frequency of the RF output is 2 MHz.

* * * * *